(12) United States Patent
Pouteau et al.

(10) Patent No.: US 12,245,614 B2
(45) Date of Patent: Mar. 11, 2025

(54) USE OF WHEY PROTEIN MICELLES FOR IMPROVING INSULIN PROFILE IN DIABETIC PATIENTS

(71) Applicant: SOCIÉTÉ DES PRODUITS NESTLÉ S.A., Vevey (CH)

(72) Inventors: Etienne Pouteau, Santiago (CL); Lionel Jean Rene Bovetto, Lucens (CH); Catherine Mace, Lausanne (CH)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 97 days.

(21) Appl. No.: 14/353,188

(22) PCT Filed: Oct. 19, 2012

(86) PCT No.: PCT/EP2012/070717
§ 371 (c)(1),
(2) Date: Apr. 21, 2014

(87) PCT Pub. No.: WO2013/057232
PCT Pub. Date: Apr. 25, 2013

(65) Prior Publication Data
US 2014/0255544 A1 Sep. 11, 2014

(30) Foreign Application Priority Data
Oct. 21, 2011 (EP) .................................... 11186144

(51) Int. Cl.
| | | |
|---|---|---|
| *A23J 1/20* | (2006.01) | |
| *A23C 21/00* | (2006.01) | |
| *A23L 2/52* | (2006.01) | |
| *A23L 2/66* | (2006.01) | |
| *A23L 33/00* | (2016.01) | |
| *A23L 33/19* | (2016.01) | |
| *A61K 35/20* | (2006.01) | |

(52) U.S. Cl.
CPC .............. *A23J 1/205* (2013.01); *A23C 21/00* (2013.01); *A23L 2/52* (2013.01); *A23L 2/66* (2013.01); *A23L 33/19* (2016.08); *A23L 33/30* (2016.08); *A23L 33/40* (2016.08); *A61K 35/20* (2013.01); *A23V 2002/00* (2013.01); *A23V 2200/00* (2013.01)

(58) Field of Classification Search
CPC ........ A23L 1/3056; A23L 1/296; A23L 33/30; A23L 33/40; A23L 2/52; A23L 2/66; A23L 33/19; A23J 1/205; A23C 21/00; A61K 35/20; A61K 9/1075; A61K 38/1709; A23V 2002/00; A23V 2200/00; A23V 2200/332; A23V 2250/54252; A23V 2200/328; A23K 20/147; A61P 3/10
USPC ........................................... 426/2, 657, 583
See application file for complete search history.

(56) References Cited

U.S. PATENT DOCUMENTS

| | | | | |
|---|---|---|---|---|
| 5,882,705 | A * | 3/1999 | Sato ..................... | A23C 9/1512 426/41 |
| 6,767,575 | B1 | 7/2004 | Huss et al. | |
| 2002/0061548 | A1* | 5/2002 | Van Beresteijn ...... | A23C 21/02 435/68.1 |
| 2002/0150649 | A1* | 10/2002 | Bell ........................ | A23L 33/30 426/2 |
| 2008/0027024 | A1* | 1/2008 | Gahler ................... | A23L 29/244 514/54 |
| 2009/0035437 | A1* | 2/2009 | Bovetto ................ | A23C 21/026 426/588 |
| 2009/0232916 | A1* | 9/2009 | Shulman ................. | A21D 2/02 424/752 |
| 2011/0250310 | A1* | 10/2011 | Mateus .................. | A23C 21/04 426/2 |

FOREIGN PATENT DOCUMENTS

| | | |
|---|---|---|
| CN | 1835760 A | 9/2006 |
| CN | 101410020 | 4/2009 |
| JP | 53050316 | 5/1978 |
| JP | 2005535339 | 11/2005 |
| JP | 2006510367 A | 3/2006 |
| WO | 2006034857 | 4/2006 |
| WO | 2007110181 A2 | 10/2007 |
| WO | 2007110411 A2 | 10/2007 |
| WO | 2007110422 A2 | 10/2007 |
| WO | 2011112695 | 9/2011 |
| WO | 2013057229 A1 | 4/2013 |

OTHER PUBLICATIONS

Chinese Office Action for Application No. 201280051704.0, dated Feb. 28, 2015, 5 pages.
New Food Industry, 2010, vol. 52, No. 1, pp. 17-23.
Baer et al. "Whey Protein but Not Soy Protein Supplementation Alters Body Weight and Composition in Free-Living Overweight and Obese Adults" The Journal of Nutrition, 2011, vol. 141, pp. 1489-1494.
Belobrajdic et al. "A High-Whey-Protein Diet Reduces Body Weight Gain and Alters Insulin Sensitivity Relative to Red Meat in Wistar Rats" The Journal of Nutrition, 2004, vol. 134, pp. 1454-1458.
Japanese Office Action for Application No. P2014-536246, Dispatch No. 254987, Dispatch Date Jun. 7, 2016, 12 pages.
Acheson et al. "Protein choices targeting thermogenesis and metabolism." The American Journal of Clinical Nutrition, 2011, vol. 93, pp. 525-534.

(Continued)

*Primary Examiner* — Erik Kashnikow
*Assistant Examiner* — Bhaskar Mukhopadhyay
(74) *Attorney, Agent, or Firm* — K&L Gates LLP

(57) ABSTRACT

The present invention relates to whey protein micelles for use in the treatment and/or prevention of a disorder linked to an increase in plasma postprandial insulin and/or plasma postprandial glucagon concentration in a subject. The invention relates also to a non-therapeutic use of whey protein micelles to decrease plasma postprandial insulin and/or glucagon concentration in healthy subjects.

3 Claims, 3 Drawing Sheets

(56) References Cited

OTHER PUBLICATIONS

Figure 1:
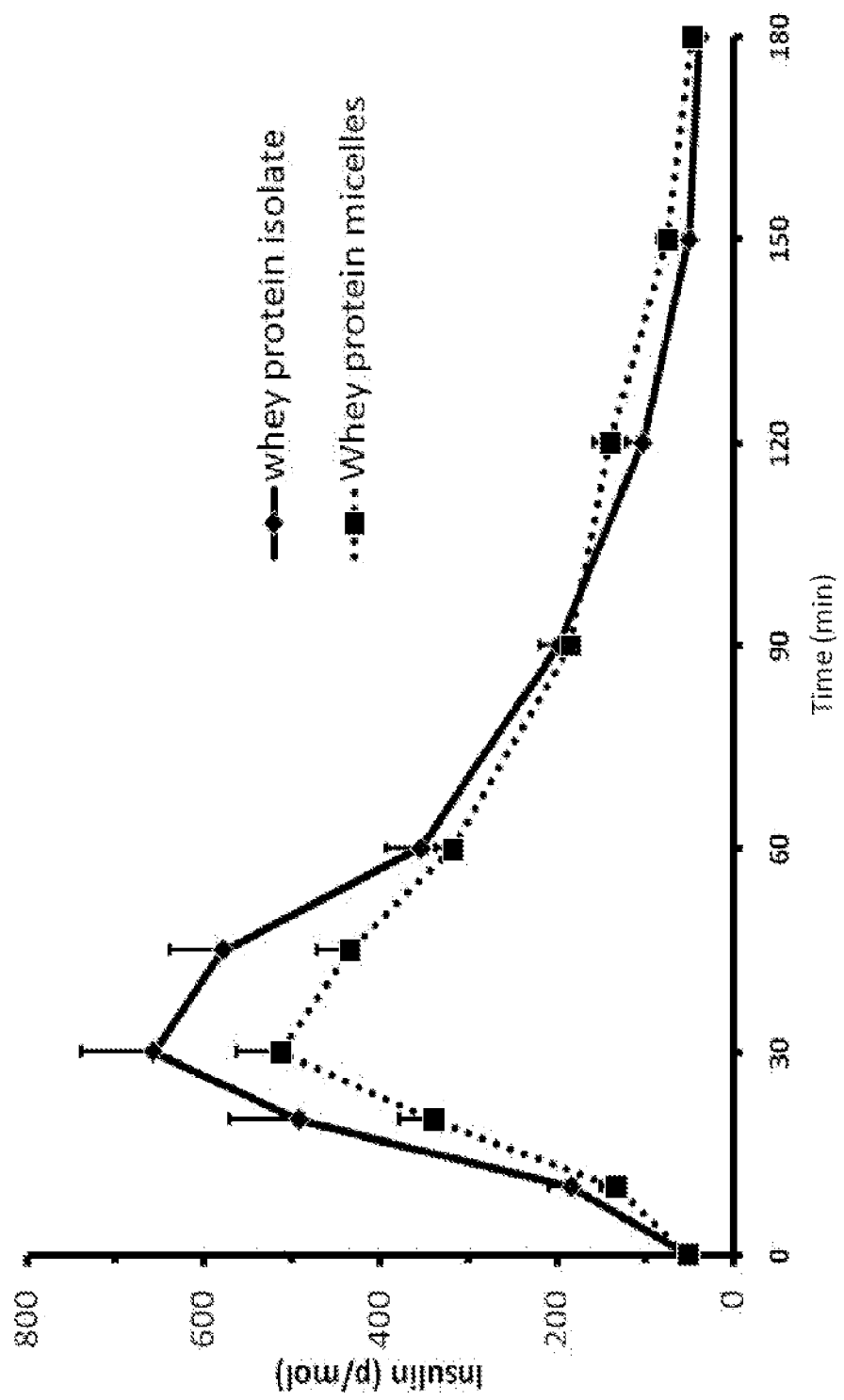

Gannon et al., "An increase in dietary protein improves the blood glucose response in persons with type 2 diabetes", Am J Clin Nutr, vol. 78, pp., 2003, pp. 734-741.

Loon et al., "Plasma insulin responses after ingestion of different amino acid or protein mixtures with carbohydrate", Am J Clin Nutr, vol., vol. 72, pp. 96-105.

Mortensen et al., "Differential effects of protein quality on postprandial lipemia in response to a fat-rich meal in type 2 diabetes: comparison of whey, casein, gluten, and cod protein", Am J Clin Nutr, vol. vol. 90, Issue 1, May 20, 2009, pp. 41-48.

Shertzer et al., "Dietary Whey Protein Lowers the Risk for Metabolic Disease in Mice Fed a High-Fat Diet", The Journal of Nutrition, Nutrition and Disease, vol. 141, 2011, pp. 582-587.

Gerich, "Is Reduced First-Phase Insulin Release the Earliest Detectable Abnormality in Individuals Destined to Develop Type 2 Diabetes?", Diabetes, vol. 51, Supplement 1, Feb. 2002, S117-S121.

Porte Jr., "Clinical importance of insulin secretion and its interaction with insulin resistance in the treatment of type 2 diabetes mellitus and its complications", Diabetes/Metabolism Research and Reviews, vol. 17, Issue 3, 2001, pp. 181-188.

Kopp, "High-Insulinogenic Nutrition—An Etiologic Factor for Obesity and the Metabolic Syndrome?", Metabolism, vol. 52, No. 7, Jul. 2003, pp. 840-844.

Lefebvre, "Glucagon and Diabetes", Handbook of Experimental Pharmacology, vol. 123, Chapter 7, 1996, pp. 115-131.

Li et al., "Study on the prevention of diabetes by whey protein in mice", Wanfang Dissertation Database, May 31, 2011 pp. 1-30 (Original copy only).

Blundell et al., Appetite Control: Methodological Aspects of The Evaluation of Foods, Obes Rev., vol. 11, No. 3, Mar. 2010, pp. 251-270.

Halford, "APPETITE/Physiological and Neurobiological Aspects", Encyclopedia of Human Nutrition, 2005, pp. 147-150.

Schmitt et al., "Internal structure and colloidal behaviour of covalent whey protein microgels obtained by heat treatment", Soft Matter, The Royal Society of Chemistry, vol. 6, 2010, pp. 4876-4884.

Stanciuc et al., "Thermal treatment can modify the susceptibility of whey protein concentrate to enzymatic hydrolysis", Innovative Romanian Food Biotechnology, vol. 7, 2010, pp. 30-36.

Shah et al., "Lack of Suppression of Glucagon Contributes to Postprandial Hyperglycemia in Subjects with Type 2 Diabetes Mellitus", The Journal of Clinical Endocrinology & Metabolism, vol. 85, No. 11, Nov. 2000, pp. 4053-4059.

Mao et al., "Dietary Fat, Insulin Resistance and Metabolic Syndrome", Foreign Medical Science, Section Hygiene, Dec. 31, 2006, pp. 73-77.

China Patent Office Communication for Application No. 201910203028.8, dated Nov. 15, 2022, 10 pages.

\* cited by examiner

USE OF WHEY PROTEIN MICELLES FOR IMPROVING INSULIN PROFILE IN DIABETIC PATIENTS

CROSS REFERENCE TO RELATED APPLICATIONS

The present application is a National Stage of International Application No. PCT/EP2012/070717, filed on Oct. 19, 2012, which claims priority to European Patent Application No. 11186144.9, filed Oct. 21, 2011, the entire contents of which are being incorporated herein by reference.

The present invention relates to whey protein micelles for use in the treatment and/or prevention of a disorder linked to an increase in plasma postprandial insulin and/or plasma postprandial glucagon concentration in a subject. The invention relates also to a non-therapeutic use of whey protein micelles to decrease plasma postprandial insulin and/or glucagon concentration in healthy subjects.

Globally it is estimated that there are about 150 million people with type-2 diabetes. The incidence varies substantially in different parts of the world, almost certainly because of genetic, nutritional, environmental and lifestyle factors. In the USA there is about 8% of the population with diabetes, with ca. 18 million patients being diagnosed, 90% of whom are type-2. With prevalence rates doubling between 1990 and 2005, the increase has been characterized as an epidemic. Traditionally considered a disease of adults, type-2 diabetes is increasingly diagnosed in children in parallel to rising obesity rates due to alterations in dietary patterns as well as in life styles during childhood.

The primary early development of diabetes may appear when insulin response to a meal or more specifically first-phase insulin release becomes abnormal (Gerich J E, 2002, Diabetes, 51:S117-S121) and elevated blood glucose becomes unavoidable over time. Then chronic hyperglycemia generates an increased insulin demand and eventually a beta-cell secretory dysfunction causing exhaustion of the beta-cells in the pancreas (Porte D J, 2001, Diabetes Metab Res Rev, 17(3):181-188). This dysfunction of the insulin secretion is believed to appear in parallel to a defect of the hepatic and peripheral insulin action, identified as the insulin resistance which induces elevated fasting blood insulin. Enhanced insulin secretion and insulin resistance both co-operate to increase insulinemia and favour the development of type-2 diabetes. As a consequence, a diminished and adequate response of the insulinemia after a meal could be the sign of an adequate insulin secretion and utilization by the body in healthy or pre-diabetic subjects. This decreased postprandial insulinemia should preserve the pancreatic function and simultaneously improve insulin sensitivity. In the long term, lowering the insulin demand after a meal might reduce (1) the risk of developing type-2 diabetes in pre-diabetic subjects and (2) the deterioration of the glycemic control in type-2 diabetes.

Proteins are known to stimulate insulin secretion and a high protein diet has the potential to lower plasma glucose and fasting triglycerides in type-2 diabetic subjects (Van Loon L J et al., 2000, Am J Clin Nutr 72:96-105; Gannon M C et al., 2003, Am J Clin Nutr 78:734-741). A recent study evaluated the acute effects of different protein types on postprandial lipemia after a fat-rich test meal in type-2 diabetic subjects (Mortensen L S et al., 2009, Am J Clin Nutr. 90:41-48). Thereby, 4 iso-caloric meals with different protein sources, i.e. whey, casein, gluten and cod protein, were compared. It was concluded that whey proteins were most effective in reducing postprandial lipemia in those patients. A further study published by Shertzer HG et al. (2011, J Nutr 141:582-587) revealed that dietary whey protein isolates administered to mice reduced the risk for metabolic disease and of developing diabetes associated with the consumption of a high-fat diet.

WO2011/112695 discloses that health benefits provided by whey proteins include control of blood glucose such that they are suitable for diabetics.

There is a persisting need in the food industry to further improve the nutritional solutions provided to diabetic subjects or subjects at risk for developing type-2 diabetes.

The object of the present invention is to improve the state of the art and to provide a new and better nutritional solution for improving the postprandial insulin and glucagon profile in a subject, particularly in a diabetic or pre-diabetic subject.

The object of the present invention is achieved by the subject matter of the independent claims. The dependent claims further develop the idea of the present invention.

Accordingly, the present invention provides in a first aspect whey protein micelles for use in the treatment and/or prevention of a disorder linked to an increase in plasma postprandial insulin and/or plasma postprandial glucagon concentration in a subject.

In a further aspect, the invention pertains to a non-therapeutic use of whey protein micelles to decrease plasma postprandial insulin and/or plasma postprandial glucagon concentration in a subject, particularly a healthy subject.

In a still further aspect, the present invention pertains to a liquid meal replacement comprising whey protein micelles.

"Whey protein micelles" are defined herein as described in EP1839492A1. Particularly, the "whey protein micelles" are the micelles comprised in the whey protein micelles concentrate obtainable by the process as disclosed in EP1839492A1.

Therein, the process for the production of whey protein micelles concentrate comprises the steps of: a) adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The "whey protein micelles" can be in liquid concentrate or in powder form. Importantly, the basic micelle structure of the whey proteins is conserved, in the concentrate, the powder and reconstituted from the powder for example in water. The "whey protein micelles" are physically stable in dispersion, as powder as well as during spray-drying or freeze-drying.

"Insulin" is a hormone secreted by the beta cells of the pancreas in response to a meal. Insulin is central to regulating carbohydrate and fat metabolism in the body.

A high insulinogenic nutrition represents a chronic stimulus to the beta cells that may induce an adaptive hypertrophy and a progressive dysregulation of the cells, resulting in postprandial hyperinsulinemia. Postprandial hyperinsulinemia may promote weight gain, fat deposition and the development of insulin resistance, metabolic syndrome, glucose intolerance and type-2 diabetes (Kopp W., Metabolism. 2003, July; 52(7):840-844).

"Glucagon" is a hormone secreted by the alpha-cells of the pancreas in response to hypoglycaemia such as during the fasting state. It is also secreted in response to a protein meal. Glucagon stimulates hepatic glucose production through an increased hepatic glycogenolysis and through an increased gluconeogenesis from lactate, glycerol or amino acids. Glucagon stimulates glucose release from the liver to the blood circulation. Glucagon is therefore another important hormone to regulate glucose in the whole body.

It has been surprisingly found by the inventors, that whey protein micelles in comparison to whey protein isolate (WPI) consumed as part of a iso-caloric and iso-nitrogenous meal replacement significantly decrease the postprandial plasma insulin response as well as the concentration of postprandial plasma glucagon. The results of a randomized double-blinded crossover clinical study are disclosed in the Example section. Previous studies have demonstrated that whey proteins in the form of WPI are most effective in reducing postprandial lipemia and reducing the risk for metabolic disease and/or development of diabetes type-2. Here, the inventors found an even better nutritional solution by providing the whey proteins in the form of whey protein micelles for the desired health benefit. Consequently, postprandial plasma insulin and/or glucagon concentrations can be lowered in comparison to WPI by providing whey protein micelles as a still further benefit to diabetic and pre-diabetic subjects.

Although not wishing to be bound by theory, the inventors think that whey protein micelles seem to induce a delayed gastric emptying or to be more slowly digested as compared to whey protein isolate (WPI). Thereby, whey protein micelles deliver the amino acids more slowly into the peripheral blood circulation. This lower amino acidemia is concomitant with a reduced insulinemia and glucagonemia compared to WPI and other dairy proteins.

FIG. 1: Plasma concentrations of insulin after the ingestion of WPM and WPI comprising meal replacements in men.

Figure 2:
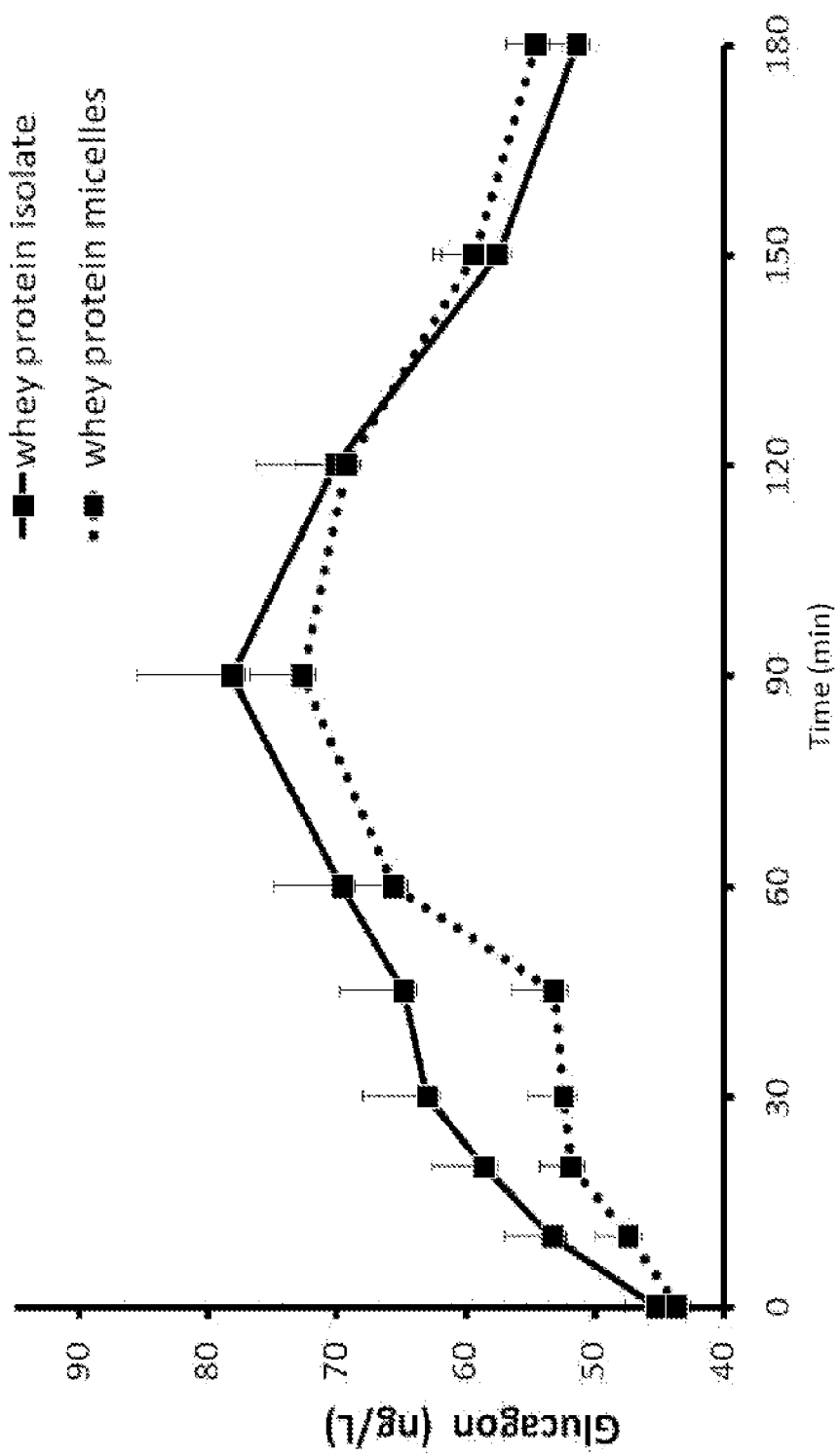

FIG. 2: Plasma concentrations of glucagon after the ingestion of WPM and WPI comprising meal replacements in men.

Figure 3:
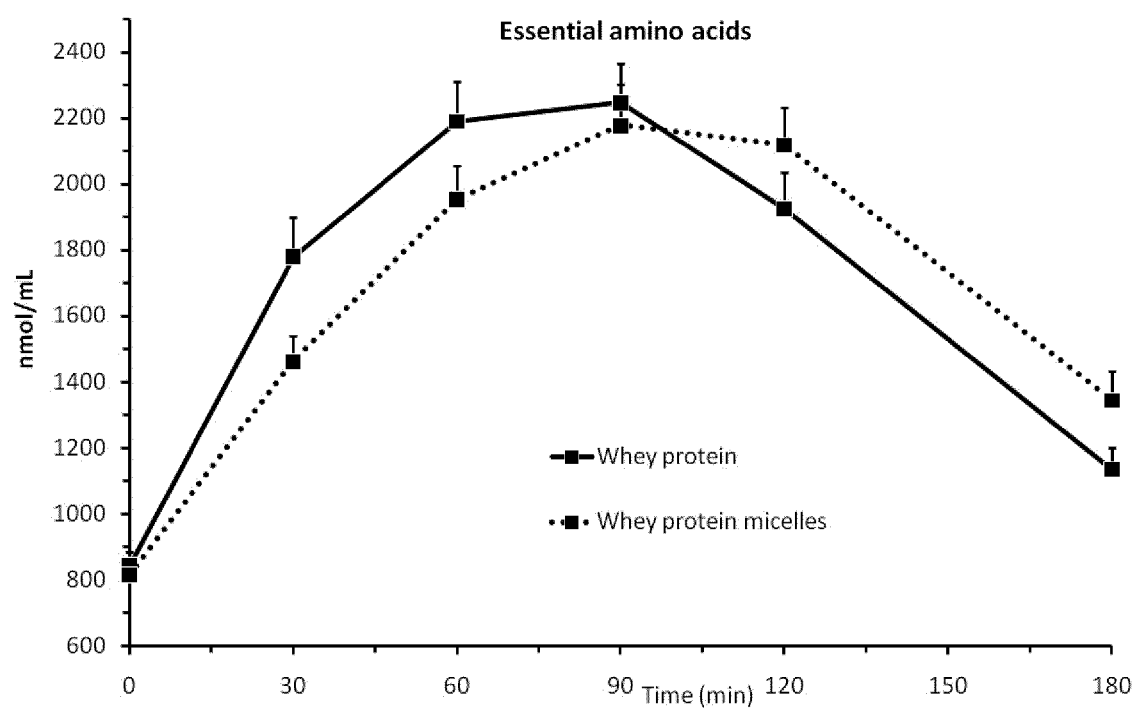

FIG. 3: Plasma concentrations of essential amino acids after the ingestion of WPM and WPI comprising meal replacements in men.

The present invention pertains to whey protein micelles for use in the treatment and/or prevention of a disorder linked to an increase in plasma postprandial insulin and/or plasma postprandial glucagon concentration in a subject, wherein the disorder is selected from the group consisting of insulin resistance, metabolic syndrome, glucose intolerance and diabetes type-2.

Typically, postprandial hyper-insulinemia may promote the development of insulin resistance, metabolic syndrome, glucose intolerance and type-2 diabetes (Kopp W., Metabolism. 2003, July; 52(7):840-844). Glucagon plasma levels are usually consistently elevated in patients with type-2 diabetes. There is also evidence that the lack of postprandial suppression of glucagon can cause postprandial hyperglycemia in type-2 diabetes (Lefebvre P, 1996, Handb Exp Pharmacol 123:115-131; Shah P et al., 2005, Int Diabetes Monitor 17:3-10). Lowering the insulin demand after a meal, however, might reduce on one hand the deterioration of the glycemic control in type-2 diabetes and on the other hand reduce the risk of developing type-2 diabetes in predisposed subjects. Hence, advantageously, the whey protein micelles are for use in the treatment and/or the prevention of insulin resistance, metabolic syndrome, glucose intolerance and diabetes type-2.

In a preferred embodiment, the whey protein micelles are for use to a diabetic or pre-diabetic patient. A "pre-diabetic patient" is a subject showing insulin resistance or impaired glucose tolerance and is predisposed, for example by family history or genetics, for developing type-2 diabetes later in life. The use of whey protein micelles would consequently reduce the risk and/or the development of insulin resistance, metabolic syndrome, glucose intolerance and type-2 diabetes in those subjects.

The whey protein micelles for use according to the invention pertains to a subject which is a human being or an animal, preferably a cat or a dog. Prevalence of diabetes type-2, insulin resistance or glucose intolerance is mostly observed in adult humans. However, more and more children are affected, or predisposed or at risk of developing such a disorder later in life. Hence, advantageously, prevention and/or treatment of those disorders is started already in young age.

Alternatively, and similarly as observed with humans, diabetes, insulin resistance and glucose intolerance is more and more widespread among animals, particularly with animals kept as pet animals. Hence, the invention preferably also pertains to cats and dogs.

In a preferred embodiment, the whey protein micelles are administered to a subject in a daily dose of at least 20 g dry weight, preferably of at least 30 g dry weight. Those doses should assure a sufficient daily quantity for providing the desired effect to a subject in at least a mid-term period.

The whey protein micelles for use according to the invention are provided as part or at the end of a regular meal. Preferentially the whey protein micelles are provided as part or at the end of a meal to confer their benefits on improving the insulin and glucagon postprandial responses in combination with that meal. An improved effect can be expected by providing the whey protein micelles directly at the end of the meal, for example as part of the dessert. Thereby, the maximal concentration of the insulin response as well as the postprandial distribution of plasma glucagon and amino acids may be further optimized.

The whey protein micelles for use according to the invention can be provided in the form of a liquid drink, a shake drink or a liquid meal replacement. As part of a major advantage of whey protein micelles is their increased solubility in water as opposed to native whey protein isolates. Thereby, liquid drinks or meal replacers can be produced which comprise about twice the amount of soluble whey proteins in comparison to where native whey protein isolate was used. This confers a significant advantage and originality for the manufacture of liquid meal replacers and meal replacement systems.

Alternatively, the whey protein micelles are provided in the form of a solid food product, for example as a bar, as flakes, as biscuits, or as pellets.

A further aspect of the present invention is the non-therapeutic use of whey protein micelles to decrease plasma postprandial insulin and/or plasma postprandial glucagon concentration in a subject, for example a healthy subject, wherein the subject is a human being or an animal, preferably a cat or a dog.

It is an advantage of the present invention that whey protein micelles can also be administered to subjects, for example healthy subjects, which perhaps may be at risk of developing diabetes type-2, insulin resistance or glucose intolerance at some later time. In fact, whey protein micelles as disclosed herein provide healthy humans and animals with a reduced insulin and glucagon plasma level after consumption of said whey protein micelles. This effect is most favourable for limiting insulin demand and potential pancreas exhaustion, while providing at the same time a sufficient amount of a high quality protein (i.e. whey) for improving the general health status of those subjects.

A still further aspect of the present invention is a liquid meal replacement comprising whey protein micelles, particularly wherein the whey protein micelles are present in an amount of at least 15 wt %, preferably of at least 20 wt % of the total dry weight of said meal replacement. In a preferred embodiment said meal replacement is for use in enteral nutrition. Thereby, advantageously, such a meal replacement can for example be used in intensive care units or hospitals, where patients due e.g. to their trauma are insulin resistant, but require a high protein diet for recovery. A liquid meal replacement thereby is very convenient and provides the required amounts of proteins in a well adapted formulation. "Enteral nutrition" herewith is defined as a way to provide food or nutrition through a tube placed in the nose, the stomach or the small intestine. Enteral nutrition is often also called tube feeding.

Those skilled in the art will understand that they can freely combine all features of the present invention disclosed herein. In particular, features described for the therapeutic use of the whey protein micelles may be combined with the non-therapeutic use, the meal replacement product, and vice versa. Further, features described for different embodiments of the present invention may be combined. Further advantages and features of the present invention are apparent from the figures and examples.

Example

The inventors discovered that whey protein micelles (WPM) decreased postprandial response of insulin in comparison to whey protein isolate (WPI) as part as a meal replacement in adult healthy men. A randomized double-blinded crossover study was performed in twenty-three healthy men. They ingested the tested meals at lunch time, separated by a wash-out period of a week. A catheter was inserted in the arm of the volunteers and served for collecting arterialized blood postprandially for 3 h. Plasma from the blood samples was used to analyze hormones (insulin, c-peptide and glucagon), glucose and amino acids.

The 2 meal replacements were iso-caloric and iso-nitrogenous. They were composed of the tested protein (30 g, 7.2% w/w), lipids (11.7 g, 2.8% w/w), carbohydrates (42.7 g, 10.2% w/w) and fibers (6.3 g, 1.5% w/w). The tested proteins were (1) WPI, whey protein isolate; and (2) WPM, whey protein micelles. The meal replacements were completed with water to 420 mL and contained 388 kcal as energy intake.

The results showed a significant decrease of the Cmax (maximal concentration, P=0.015) of insulin responses after the ingestion of the WPM compared with the WPI meal replacements. FIG. 1 shows the mean postprandial insulin responses after the meal replacement ingestion. The development over time of the glucagon postprandial response was improved after the WPM meal compared the WPI meal (FIG. 2). Surprisingly, the WPM meal replacement induced the lowest concentration of plasma amino acids 30 min after the meal ingestion, as opposed to the other protein meal (FIG. 3). The WPM exhibits the lowest rate of rise of essential amino acids in the systemic blood circulation. These lowest plasma amino acids probably participate in lowering the plasma insulin and glucagon responses of the WPM at 30 min, the time of insulin Cmax.

This study showed the advantage of WPM in lowering plasma insulin as well as glucagon compared with WPI in healthy men.

The invention claimed is:

1. A method for decreasing plasma postprandial insulin and plasma postprandial glucagon concentration in a human subject, the method comprising administering to the human subject a nutrition composition that is a meal replacement comprising a daily dose of whey protein micelles 30 g dry weight, lipids 11.7 g dry weight, carbohydrates 42.7 g dry weight, and fibers 6.3 g dry weight in,
   wherein the meal replacement is a liquid food product, and the meal replacement decreases the plasma postprandial insulin and the plasma postprandial glucagon concentration relative to a composition containing an equal amount of whey protein isolate.

2. The method according to claim 1, wherein the whey protein micelles are the only protein in the meal replacement.

3. The method according to claim 1, wherein the meal replacement induces a lower concentration of plasma amino acids thirty minutes after ingestion relative to a composition containing an equal amount of whey protein isolate.

* * * * *